United States Patent [19]

Kokubun et al.

[11] Patent Number: 5,456,746
[45] Date of Patent: Oct. 10, 1995

[54] HARD FILM COMPOSITION FOR CAPSULES

[75] Inventors: Toshio Kokubun, Tokyo; Hiroshi Ohnuki, Yokohama; Toyokazu Shimizu, Sagamihara, all of Japan

[73] Assignee: Warner-Lambert Company, Morris Plains, N.J.

[21] Appl. No.: 153,519

[22] Filed: Nov. 16, 1993

[30] Foreign Application Priority Data

Nov. 30, 1992 [JP] Japan .................................. 4-319583

[51] Int. Cl.$^6$ .................................................. C09D 189/00
[52] U.S. Cl. ........................................ 106/131; 106/132
[58] Field of Search ................................... 106/131, 132

[56] References Cited

U.S. PATENT DOCUMENTS

| 2,346,928 | 4/1944 | Lighthipe ................................. 106/131 |
| 3,000,835 | 9/1961 | Mayhew et al. ......................... 106/132 |
| 4,576,645 | 3/1986 | Ravel et al. ............................. 106/131 |
| 4,601,896 | 7/1986 | Nugent ..................................... 106/131 |
| 4,877,454 | 10/1989 | Charkoudian .......................... 106/131 |

FOREIGN PATENT DOCUMENTS

| 0092908 | 11/1983 | European Pat. Off. ......... C08L 89/06 |
| 8700429 | 1/1987 | WIPO ................................ A01K 9/48 |

OTHER PUBLICATIONS

Database WPI Week 9247 Derwent Publications Ltd., London, GB; An 92-387686 & JP-A-4 288 012 (Tokai Capsule KK) *abstract* (1992) No Month Avail.

Primary Examiner—David Brunsman
Attorney, Agent, or Firm—Charles W. Almer

[57] ABSTRACT

A hard film composition for capsules comprising a gelatin, from 3 to 10% by weight of an ester of a fatty acid and glycerol or polyglycerol. The capsules formed by the composition of the invention are not embrittled when the moisture in the capsule film is reduced by charging therein a hygroscopic drug, Consequently, cracking and chipping of the capsule are reduced and leakage from the capsule caused by such damage is also reduced.

10 Claims, No Drawings

HARD FILM COMPOSITION FOR CAPSULES

BACKGROUND OF THE INVENTION

1. Field of the Invention

The present invention relates to a hard film composition for capsules to be used for forming hard gelatin capsules and for band sealing such hard gelatin capsules.

2. Description of Related Art

Hard gelatin capsules are widely utilized in the field of pharmaceutical preparations due to ease of preparation and administration. However, conventional hard gelatin capsules have a problem in that the capsule film loses flexibility and suffers cracking or chipping if the capsules are packed with a hygroscopic agent, such as a powder or granular material, since the moisture contained in the capsule film is absorbed by the drug. Particularly, capsules are most commonly damaged when they are filled with such a drug and packaged or when they are taken out of the package for administration. Accordingly, limited types of drugs may be contained in conventional hard gelatin capsules in order to prevent embrittlement of the capsule films caused by moisture reduction.

Also known in the art are hard film compositions for hard gelatin capsules having flexibility which is increased by adding a plasticizer, such as glycerol, sorbitol, or polyethylene glycol to the gelatin. However, such hard gelatin capsules suffer problems in capsule manufacture in that the capsule films become too soft and the capsule drying speed is retarded due to the added plasticizer.

It is an object of the present invention to provide a hard film composition for capsules which will not be embrittled by a reduction in the moisture in the capsule film, even when a hygroscopic drug is contained in the capsule. Further, the present invention minimizes the cracking and chipping of the capsules and thus prevents leakage of the drug contained within the capsules.

SUMMARY OF THE INVENTION

The present invention is directed to a hard film composition for capsules, comprising a gelatin and 3 to 10% by weight of an ester of a fatty acid and glycerol or a polyglycerol.

The capsules formed by the composition of the invention are not embrittled when the moisture in the capsule film is reduced by charging therein a hygroscopic drug. Consequently, cracking and chipping of the capsule are reduced and leakage from the capsule caused by such damage is also reduced.

DETAILED DESCRIPTION OF THE INVENTION

The present invention is directed to a hard film composition for gelatin capsules which employs an ester of a fatty acid and a glycerol. The ester of a fatty acid and glycerol to be employed in the hard film composition can be exemplified by esters of fatty acids of edible oil or fat origin and glycerol and derivatives thereof, as described in the Official Regulation on Food Additives. The fatty acids to be employed need not be limited so long as they are of edible oil or fat origin and include, for example, saturated fatty acids such as palmitic acid and stearic acid or unsaturated fatty acids such as oleic acid and linoleic acid.

Preferred esters of glycerol and fatty acids are monoglyceride and a mixture of monoglyceride and diglyceride, which primarily contains monoglyceride (distilled monoglyceride). Preferred among these esters of fatty acids and glycerol are glycerol monofatty acid esters, glycerol acetate fatty acid esters, glycerol lactate fatty acid esters, glycerol citrate fatty acid esters, glycerol succinate fatty acid esters, glycerol diacetyltartrate fatty acid esters and glycerol monoacetate. Further, derivatives of the monoglyceride reacted with acetic acid, lactic acid, citric acid, succinic acid or diacetyltartaric acid may also be included in the ester of a fatty acid and glycerol.

Pursuant to the invention, the ester of a fatty acid and a polyglycerol includes esters of a polyglycerol obtained by polymerization of 2 to 10 moles of the glycerol and fatty acids. Also included are esters of a polyglycerol with a condensed licinoleic acid obtained by condensation of 2 to 3 moles of licinoleic acid. Preferred esters include polyglycerol monofatty acid esters and polyglycerol condensed licinoleate.

The ester of a fatty acid and glycerol or a polyglycerol is preferably added in an amount of 3 to 10% by weight and most preferably in an amount of 5% by weight based on the gelatin. If the ester is added in an amount of less than 3% by weight, brittleness of the resulting capsules may not be improved, whereas if the ester is added in an amount of more than 10% by weight the resulting capsules may occasionally be unfavorably deformed.

The hard film composition of the present invention may be prepared by known conventional methods. For example, a capsule manufacturing composition may be prepared by adding a predetermined amount of glycerol fatty acid ester to an aqueous gelatin solution and then supplying the resulting composition to a capsule manufacturing machine to form capsules. If a hydrophilic glycerol fatty acid ester is to be added to the aqueous gelatin solution, it is preferably added after emulsification of the ester to an O/W type emulsion. Further, when the ester of a fatty acid and glycerol or a polyglycerol is added to the gelatin, titanium oxide, a coloring agent such as a dye, and other known additives may also be added thereto.

A fuller understanding of the present invention will be gained from a review of the following illustrative example. Unless otherwise specified, all amounts are expressed in percent by weight.

EXAMPLE

A glycerol acetic acid fatty acid ester, warm water and an aqueous gelatin solution were mixed at a volume ratio of 2:3:5, and the resulting mixture was emulsified using a commercially available emulsifying machine to provide an O/W type dispersion. The dispersion was added to a 34% aqueous gelatin solution prepared by dissolving a gelatin powder in warm water such that the amount of dispersion was 5% of the gelatin. A coloring agent, titanium oxide was added thereto, and the viscosity was adjusted to provide a composition suitable for capsule manufacturing. The composition was then supplied to the capsule manufacturing machine to make hard capsules. The capsule thus obtained were subjected to three tests. Control capsules containing no glycerol fatty acid ester were also used in each test.

One test performed was an empty capsule crack test. In this test, capsules were tested using a Frank tester, manufactured by Carl Frank GmbH. The test was performed by measuring the percentage of cracked capsules in 50 capsules when the power at cracking was set at 0.5 J. The results of the empty capsule crack test are set forth in Table 1.

TABLE 1

Empty Capsule Crack Test (Unit: %)

| Capsule water content (%) | 13% | 11% | 9% | 8% |
|---|---|---|---|---|
| Capsule of the invention | 0 | 21 | 61 | 85 |
| Control capsule | 1 | 45 | 89 | 99 |

A second test performed was a packed capsule pressurization test. For this test, the capsule were packed with a corn starch and a load of 5 kg. was applied thereto to determine the proportion of broken capsules in the 50 capsules tested. The test results of the packed capsule pressurization test are set forth in Table 2.

TABLE 2

Packed Capsule Pressurization Test (Unit: %)

| Capsule water content (%) | 13% | 11% | 9% | 8% |
|---|---|---|---|---|
| Capsule of the invention | 0 | 0 | 2.9 | 11.8 |
| Control capsule | 0 | 2.7 | 10.9 | 26.8 |

A third test performed was a disintegration test. For this test, according to the Pharmacopoeia of Japan (Revision XII), capsules packed with lactose were immersed in distilled water at 37 (+)(−)2 C. The times until the capsules ruptured, until the contents were released and until the capsules were fully dissolved were measured. The results of the disintegration test are set forth in Table 3.

TABLE 3

Disintegration Test (Unit: seconds)

| | Time until ruptured | Time until released | Time until dissolved |
|---|---|---|---|
| Capsule of invention | 53 | 110 | 672 |
| Control capsule | 46 | 108 | 751 |

As clearly shown in Tables 1 and 2, the capsules obtained using the composition of the present invention have excellent capsule strength, particularly in the low moisture range when compared with conventional capsules and the control capsules. Table 3 shows that the present capsules have the same disintegrativity as that of conventional capsules.

The purpose of the above description is to illustrate some embodiments of the present invention, without implying any limitation. It will be apparent to those skilled in the art that various modifications and variations may be made without departing from the spirit or scope of the invention.

We claim:

1. A hard film composition for capsules, comprising a gelatin and from about 5% to about 10% by weight based on said gelatin of an ester of a fatty acid and glycerol.

2. A hard film composition for capsules according to claim 1 wherein the ester is esterified with aliphatic saturated or unsaturated mono- or dicarboxylic acids containing up to 10 atoms.

3. A hard film composition for capsules according to claim 2, wherein the fatty acid is selected from the group consisting of edible oil, fat, and hydrogenated products thereof.

4. A hard film composition for capsules according to claim 3, wherein the fatty acid is selected from the group consisting of palmitic acid, stearic acid, oleic acid, rinoleic acid and ricinoleic acid.

5. A hard film composition according to claim 1, wherein the ester of fatty acid and glycerol is selected from the group consisting of monoglyceride, diglyceride, glycerol monofatty acid esters, glycerol acetate fatty acid esters, glycerol lactate fatty acid esters, glycerol citrate fatty acid esters, glycerol succinate fatty acid esters, glycerol diacetyltartrate fatty acid esters and glycerol monoacetate.

6. A hard film composition according to claim 5, wherein the ester of fatty acid and glycerol is a derivative of monoglyceride reacted with an acid.

7. A hard film composition according to claim 6, wherein the acid is selected from the group consisting of acetic acid, lactic acid, citric acid, succinic acid and diacetyltartaric acid.

8. A hard film composition for capsules, comprising a gelatin, from about 5% to 10% by weight based on said gelatin of an ester of a fatty acid, and a polyglycerol, wherein the polyglycerol is obtained by polymerization of about 2 to about 10 moles of glycerol and the polyglycerol is esterified with a fatty acid of a condensed ricinoleic acid.

9. A hard film composition according to claim 8, wherein the glycerol is esterified with polyglycerol monofatty acid ester and polyglycerol condensed ricinoleate.

10. A hard film composition according to claim 8, wherein the esters of fatty acid and polyglycerol are selected from the group consisting of polyglycerol monofatty acid esters and polyglycerol condensed ricinoleate.

* * * * *